US00PP11266P

United States Patent [19]

Meewisse

[11] Patent Number: Plant 11,266

[45] Date of Patent: Mar. 7, 2000

[54] SCHEFFLERA PLANT NAMED 'PARADISE'

[76] Inventor: Franciscus J. M. Meewisse, Tuindershof 31, 7887 TA Erica, Netherlands

[21] Appl. No.: 09/004,817

[22] Filed: Jan. 9, 1998

[51] Int. Cl.[7] ..... A01H 5/00

[52] U.S. Cl. ..... Plt./377

[58] Field of Search ..... Plt./377

*Primary Examiner*—Howard J. Locker
*Assistant Examiner*—Kent L. Bell
*Attorney, Agent, or Firm*—C. A. Whealy

[57] ABSTRACT

A distinct cultivar of Schefflera plant named 'Paradise', characterized by its upright plant habit; rapid growth rate; closely-spaced leaves and short petioles which give a dense and full appearance; and very glossy and dark green leaflets.

2 Drawing Sheets

The present invention relates to a new and distinct cultivar of Schefflera plant, botanically known as *Schefflera arboricola,* and hereinafter referred to by the cultivar name 'Paradise'.

The new cultivar was discovered by the inventor in a controlled environment in Erica, The Netherlands, in June, 1992, as a naturally-occurring mutation of the *Schefflera arboricola* cultivar 'Amate' (not patented). The new cultivar was observed as a single plant in a group of plants of the parent cultivar. Compared to plants of the parent cultivar, plants of the new Schefflera are more compact, denser, and have shorter petioles and thicker stems. In addition, plants of the new Schefflera differ from the plants of the parent cultivar in leaf shape.

Asexual propagation of the new cultivar by terminal cuttings taken in a controlled environment in Erica, The Netherlands, has shown that the unique features of this new Schefflera are stable and reproduced true to type in successive generations.

The new Schefflera has not been observed under all possible environmental conditions. The phenotype may vary somewhat with variations in environment such as temperature and light intensity, without, however, any variance in genotype.

The following traits have been repeatedly observed and are determined to be the unique characteristics of plants of the new Schefflera. These characteristics in combination distinguish the new Schefflera as a new and distinct cultivar:

1. Upright plant habit.
2. Rapid growth rate.
3. Closely-spaced leaves and short petioles which give a dense and full appearance.
4. Very glossy and dark green leaflets.
5. Unattractive to aphids, spider mites and thrips.

BRIEF DESCRIPTION OF THE PHOTOGRAPHS

The accompanying colored photographs illustrate the overall appearance of the new Schefflera, showing the colors as true as it is reasonably possible to obtain in colored reproductions of this type.

The photograph on the first sheet comprises a top perspective view of a typical potted plant of the new Schefflera.

The photograph on the second sheet comprises a close-up view of a typical leaf of the new Schefflera. Leaf colors in the photographs may differ from actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe six-month old plants in 30-cm containers grown in Erica, The Netherlands, under commerical practice in a glass-covered greenhouse with day and night temperatures averaging 23° C. and 21° C., respectively. Average light level was 50 watt/cm$^2$.

Botanical classification: *Schefflera arboricola* cultivar 'Paradise'.

Parentage: Naturally-occurring mutation of *Schefflera arboricola* cultivar 'Amate' (not patented).

Propagation:

*Type.*—By terminal cuttings.

*Time to initiate roots.*—Winter: About 35 days at 23° C. Summer: About 30 to 35 days at 28° C.

*Rooting habit.*—Numerous, fleshy and thick.

Plant description:

*Plant shape.*—Mostly erect and upright, inverted triangle, symmetrical.

*Growth habit.*—Bushy, dense and full.

*Plant height.*—About 80 to 100 cm from soil level to top of leaf plane.

*Plant vigor/crop time.—High, rapid growth rate under optimum temperatures. Appropriate for* 19-cm and larger containers. About 25 weeks are required to produce 90-cm tall plants.

*Stem description.*—Shape: Nearly round with small lenticels about 3 mm in length. Internode length: 7 cm maximum. Color: 144A with slight reddish tones.

*Foliage description.*—Radially compound leaves. Number of leaflets per leaf: Usually about seven or eight. Leaf diameter: About 40 to 60 cm. Leaf petiole: Cross-section: Round. Length: About 4 to 12 cm. Diameter: About 1 cm. Color: 144A, slight reddish tones. Leaflet shape: Oblanceolate. Leaflet length: About 30 cm. Leaflet width: About 12 cm. Margin: Entire. Leaflet apex: Apiculate. Leaflet base: Acute. Leaflet texture: Leathery, thick, smooth, very glossy, glabrous and durable. Leaflet color: Upper surface: Glossy, dark green, 137A. Lower surface: 147C/147D. Venation: 145A. Leaflet petiole: Cross-section: Flat, round. Length: About 6 to 9 cm. Diameter: About 3 to 5 mm. Color: 144A, slight reddish tones on upper surface.

Flower description: Flowers have not been observed on plants of the new Schefflera.

Disease/insects resistance: No known Schefflera diseases observed to date on plants grown under commerical shadehouse conditions. Aphids, spider mites and thrips are not attracted to plants of the new Schefflera.

It is claimed:

1. A new and distinct cultivar of Schefflera plant named 'Paradise', as illustrated and described.

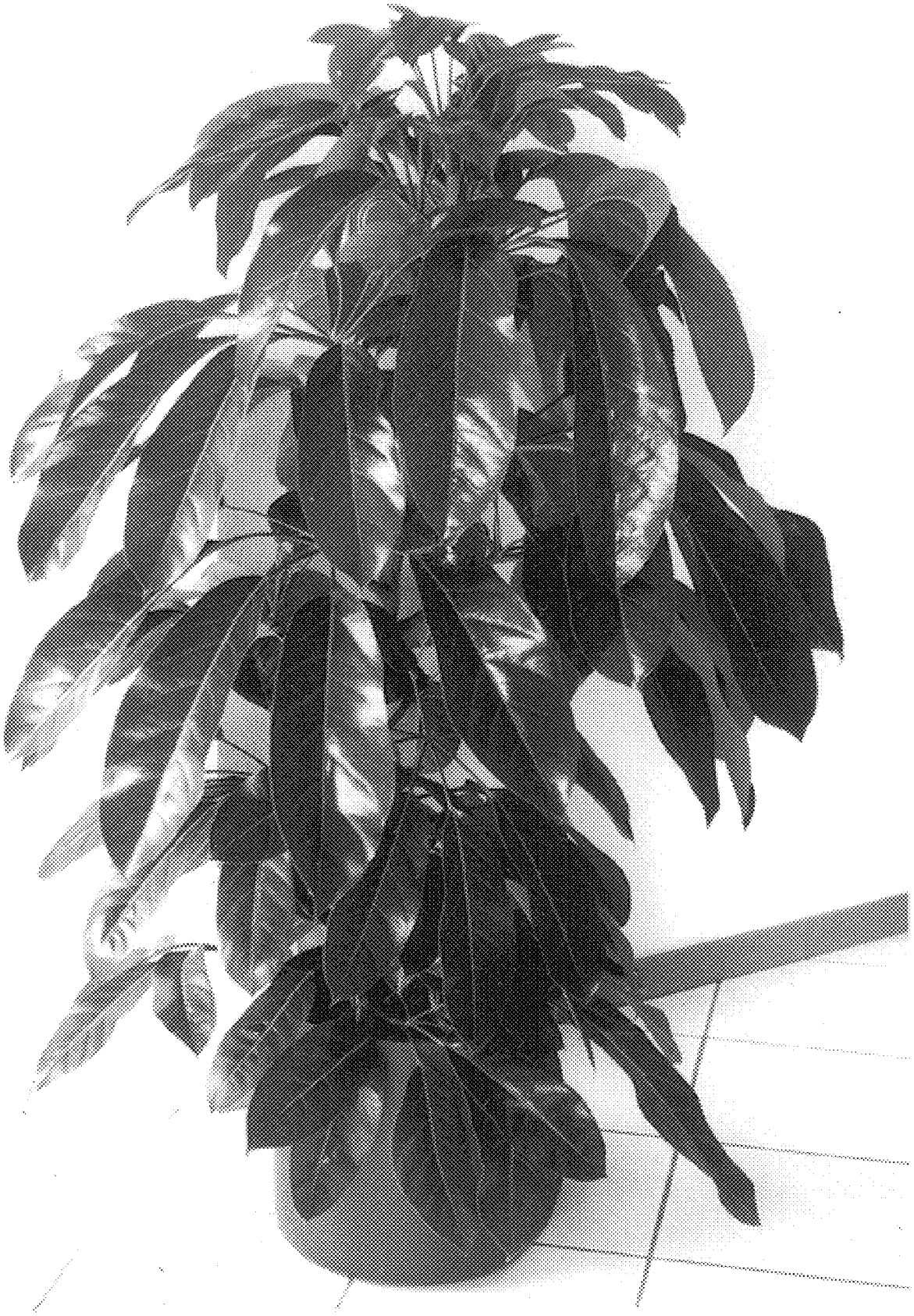

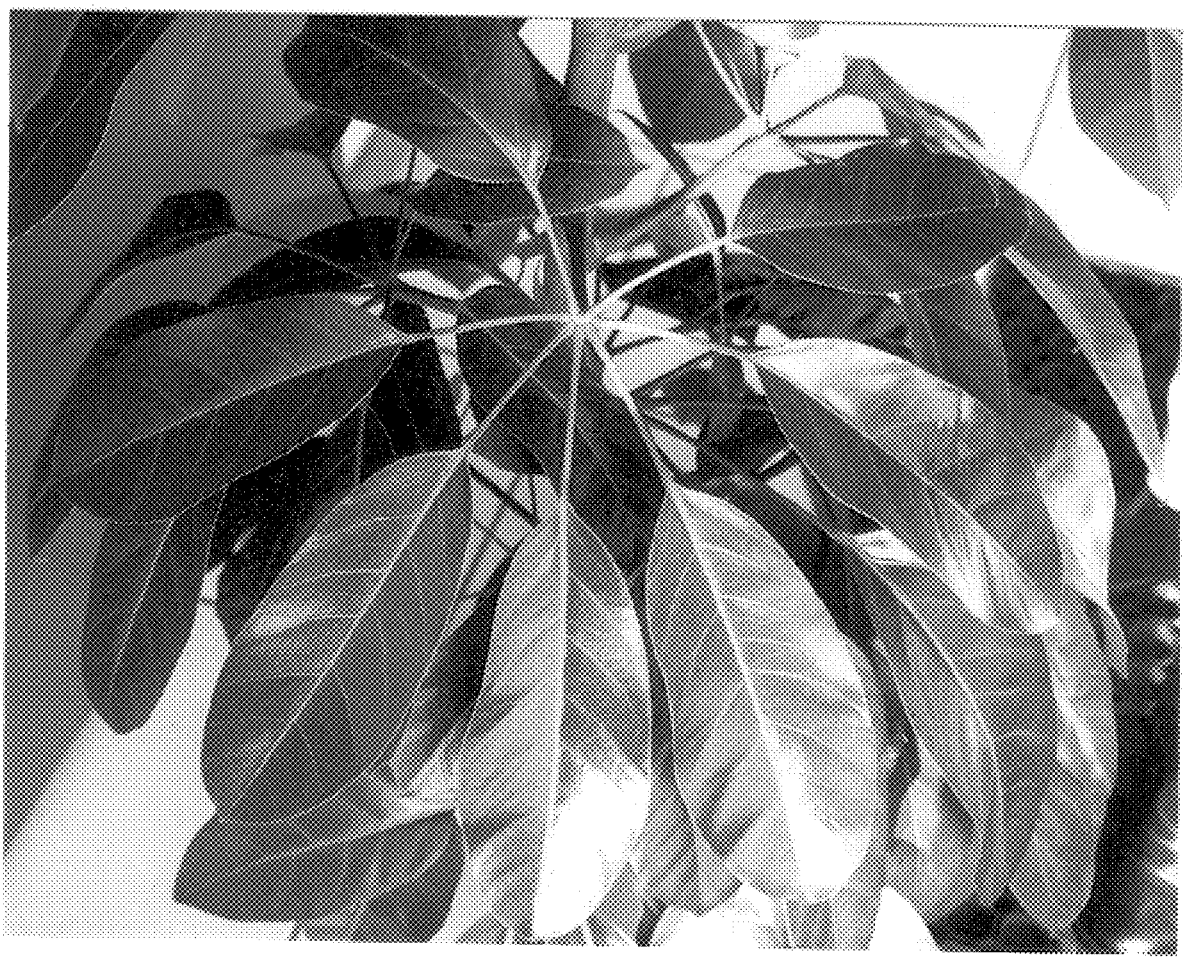

* * * * *